(12) United States Patent
Choi et al.

(10) Patent No.: US 7,642,075 B2
(45) Date of Patent: Jan. 5, 2010

(54) PROCESS OF PREPARING A BIODEGRADABLE POLYMER USING AN ENZYME CATALYST AND A BIODEGRADABLE POLYMER PREPARED THROUGH THE PROCESS

(75) Inventors: Insung S. Choi, Daejeon (KR); Kuk Ro Yoon, Chungcheongnam-do (KR)

(73) Assignee: Korea Advanced Institute of Science and Technology, Taejon (KR)

( * ) Notice: Subject to any disclaimer, the term of this patent is extended or adjusted under 35 U.S.C. 154(b) by 0 days.

(21) Appl. No.: 10/974,118

(22) Filed: Oct. 27, 2004

(65) Prior Publication Data

US 2006/0039980 A1 Feb. 23, 2006

(30) Foreign Application Priority Data

Aug. 19, 2004 (KR) .................... 10-2004-0065551

(51) Int. Cl.
*C12P 7/62* (2006.01)
*A61K 9/14* (2006.01)
(52) U.S. Cl. .................... 435/135; 424/486; 435/198
(58) Field of Classification Search ................ 435/135, 435/142, 158, 134
See application file for complete search history.

(56) References Cited

U.S. PATENT DOCUMENTS

| 5,147,791 | A | * | 9/1992 | Morrow et al. ............... 435/123 |
| 5,273,898 | A | * | 12/1993 | Ishii ............................ 435/198 |
| 5,631,343 | A | * | 5/1997 | Binns et al. .................. 528/274 |
| 6,165,602 | A | * | 12/2000 | Fujita .......................... 428/216 |

OTHER PUBLICATIONS

Yadong Wang, et al., A Tough Biodegradable Elastomer, Nature Biotechnology, vol. 20, Jun. 2002.

* cited by examiner

*Primary Examiner*—Herbert J. Lilling
(74) *Attorney, Agent, or Firm*—Lucas & Mercanti, LLP

(57) ABSTRACT

Disclosed is a process of preparing a biodegradable polymer using an enzyme catalyst and a biodegradable polymer prepared through the process. The process includes polycondensing a polyhydric alcohol monomer having a secondary hydroxyl functional group and an acid monomer having a dicarboxylic group in the presence of the enzyme catalyst. Since the biodegradable polymer according to the present invention is polymerized using an enzyme in the course of the polycondensation, it is easily prepared and friendly to nature, and it is possible to control the molecular weight by varying the reaction time in the course of the polymerization. Thus, the biodegradable polymer is usefully applied to control the dose of a drug in a drug release system and is useful as a supporter for regenerating a desired biological tissue of a patient in tissue engineering.

6 Claims, 3 Drawing Sheets

[Figure 1]
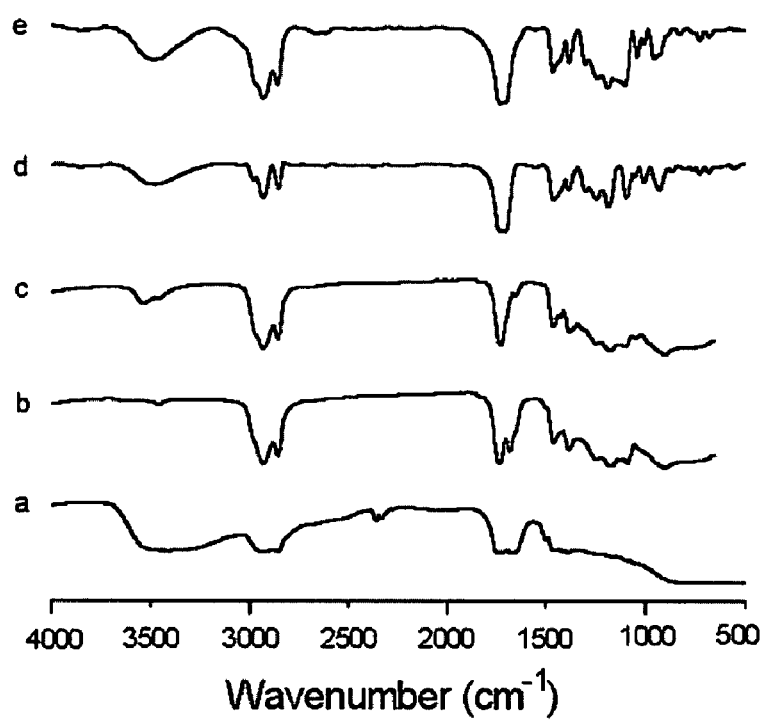
a : poly(glycerol-sebacate)
b : poly(propane-1,2-diol-sebacate)
c : poly(butane-1,3-diol-sebacate)
d : poly(butane-2,3-diol-sebacate)
e : poly(pentane-2,4-diol-sebacate)

[Figure 2]
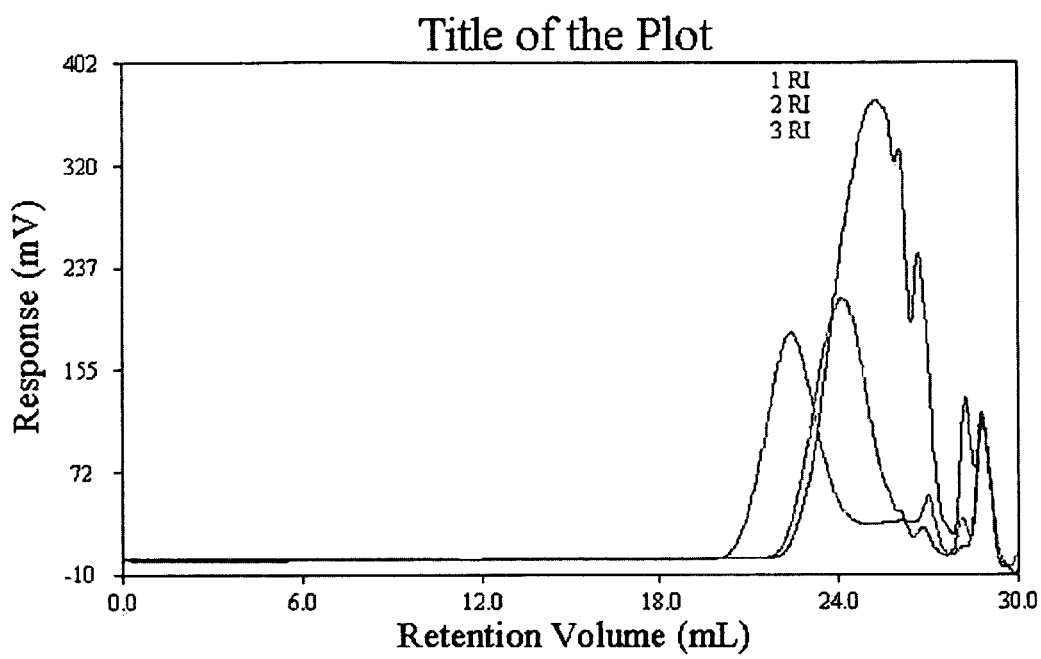
1RI : poly(glycerol-sebacate)
2RI : poly(propane-1,2-diol-sebacate)
3RI : poly(butane-1,3-diol-sebacate)

[Figure 3]
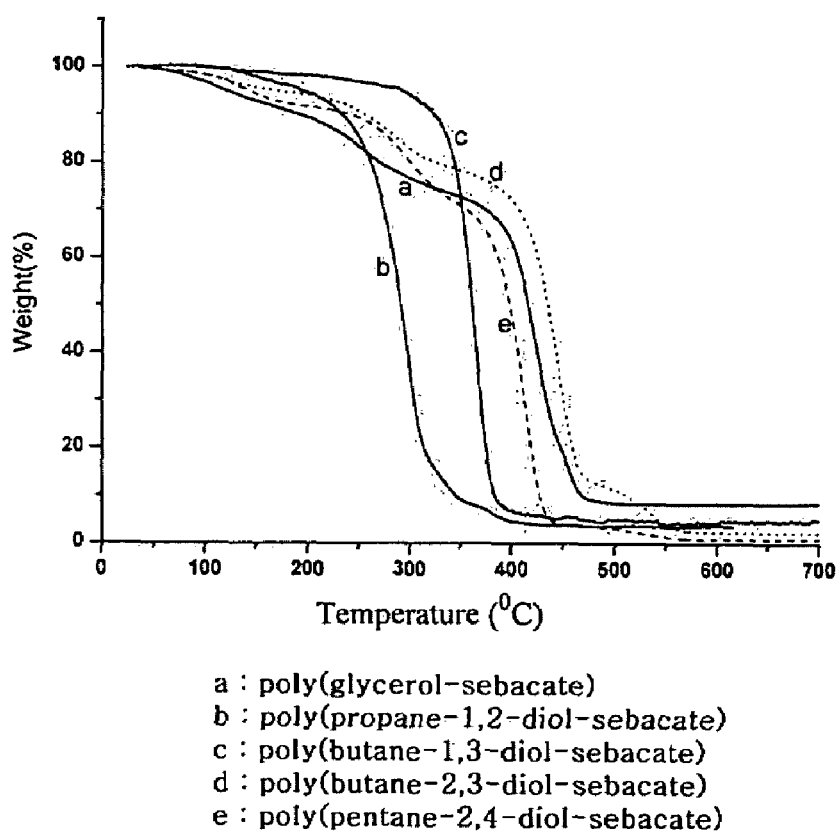
a : poly(glycerol-sebacate)
b : poly(propane-1,2-diol-sebacate)
c : poly(butane-1,3-diol-sebacate)
d : poly(butane-2,3-diol-sebacate)
e : poly(pentane-2,4-diol-sebacate)

US 7,642,075 B2

PROCESS OF PREPARING A BIODEGRADABLE POLYMER USING AN ENZYME CATALYST AND A BIODEGRADABLE POLYMER PREPARED THROUGH THE PROCESS

This patent application claims the benefit of priority from Korean Patent Application No. 10-2004-0065551 filed Aug. 19, 2004 the contents of which are incorporated herein by reference.

BACKGROUND OF THE INVENTION

1. Field of the Invention

The present invention relates to a process of preparing a biodegradable polymer using an enzyme catalyst and a biodegradable polymer prepared through the process.

2. Description of the Prior Art

A biodegradable polymer exemplified by poly($\epsilon$-caprolactone), poly(glycolic acid), poly(lactic acid), polyorthoester, polyphosphagene, and polypeptide is an polymer capable of being decomposed in vivo by a simple hydrolysis or enzyme action.

The melting point of poly($\epsilon$-caprolactone) is a low 59-64° C. and it has excellent solubility, and thus, it is mixed with other substances to be used as a biological substance. Furthermore, since it has a very slower biodegradation speed than poly(glycolic acid) or poly(lactic acid), it may be usefully applied to drug delivery system fields.

Since most biodegradable polymers are expensive, they are most often used as a high value-added medical material applied to an absorbent suture for stitching a wound, a tissue bonding agent, a bone grafting material, a drug delivery body, a tissue engineering or the like.

In a laboratory of Kobayashi Shiro, a professor of Kyoto University taking the initiative in studying the above field, with the development of a crystalline polymer "polyphenyleneoxide (PPO)" having superior heat resistance to polyphenylenesulfide (PPS) and generating only water as a byproduct at a low temperature of 40° C. and atmospheric pressure, commercialization of a "phenol resin containing an acetylene group" developed in partnership with Northeast Alps Co. has almost been completed. Furthermore, the laboratory is studying a process of preparing an polymer having superior properties to conventional polymer under moderate reaction conditions.

A process of preparing a biodegradable polymer is well known in the art, and Yadong Wang et al. suggest a process of preparing poly(glycerol-sebacate) (PGS) belonging to a biodegradable polymer which includes polycondensing glycerol and sebacic acid in the presence of a metal catalyst (Yadong Wang, Guillermo A. Ameer, Barbara J. Sheppard, Robert Langer, Nature Biotechnology, vol. 20, June 2002, 602-606). However, this process is problematic in that it is difficult to apply the process to humans because of use of a metal catalyst, and a complicated process, for example heating under reduced pressure, must be carried out.

In the course of studying development of a simple process which is not toxic to humans, many efforts have been focused on the production of a biodegradable polymer using an enzyme as a catalyst. Because the production of polymers using enzymes as catalysts is considered to help control specific polymer structure and expand functionality, many studies have been conducted worldwide. In detail, much effort has been made to develop a heat-resistant polymer, modify a conventional process of preparing a plastic, and provide novel functions in application fields.

An enzyme catalytic reaction is characterized in that the reaction is conducted at low temperatures and atmospheric pressure, a small amount of byproducts is generated, and only water and carbon dioxide are generated according to circumstances unlike a conventional polymerization reaction. The method of preparing a polymer having high performance and an polymer intermediate through an environmentally friendly enzyme-oxygen process is available, and an expectation of early commercialization of the method is growing.

Additionally, a promising organic reaction using an enzyme in vitro has aroused interest. The organic reaction using the enzyme is known to have the following three characteristics: one is that the reaction is carried out under moderate temperature, pressure, and pH conditions and energy efficiency is considered high, another is that it is possible to develop a novel reaction using regular stereochemistry in the pharmaceutical or agricultural chemistry fields, and the third is that a natural catalyst harmless to humans is employed, as is required in a green chemistry field.

The conventional process of preparing an polymer using an enzyme is classified into ring-open polymerization using lactones, polycondensation using diacid derivatives and diol, and polycondensation using hydroxyacid and ester. A lipase-catalysed acylation and elimination reaction is known as a case of an enzyme being used as a catalyst in a chemical reaction, and the enzyme is of high utility as a catalyst that is harmless to humans in the course of preparing substances applied to humans. However, in the case of polycondensation using diacid derivatives and diol, only diol having a primary alcohol group was used, but secondary alcohol has been scarcely studied.

Accordingly, the present inventors conducted a polycondensation of a polyhydric alcohol monomer having a secondary hydroxyl functional group and an acid monomer having a dicarboxylic group in the presence of an enzyme catalyst to prepare a biodegradable polymer, resulting in the finding that the biodegradable polymer is friendly to nature and it is possible to control the molecular weight by varying the reaction time in the course of the polymerization, thereby accomplishing the present invention.

SUMMARY OF THE INVENTION

Therefore, an object of the present invention is to provide a process of preparing a biodegradable polymer using an enzyme catalyst.

Another object of the present invention is to provide a biodegradable polymer prepared according to the above process.

BRIEF DESCRIPTION OF THE DRAWINGS

The above and other objects, features and other advantages of the present invention will be more clearly understood from the following detailed description taken in conjunction with the accompanying drawings, in which:

FIG. 1 illustrates FT-IR spectrum results of a biodegradable polymer according to the present invention;

FIG. 2 illustrates gel permeation chromatography (GPC) results of the biodegradable polymer according to the present invention; and FIG. 3 illustrates thermogravimetric analysis (TGA) results for the biodegradable polymer according to the present invention.

DETAILED DESCRIPTION OF THE INVENTION

The present invention provides a process of preparing a biodegradable polymer using an enzyme catalyst.

Additionally, the present invention provides a biodegradable polymer prepared according to the above process.

Hereinafter, a detailed description will be given of the present invention.

The process of preparing the biodegradable polymer according to the present invention includes polycondensating a polyhydric alcohol monomer having a secondary hydroxyl functional group and an acid monomer having a dicarboxylic group in the presence of an enzyme catalyst, which is carried out according to the following Scheme 1.

<Scheme 1>

(a) poly(glycerol-sebacate)

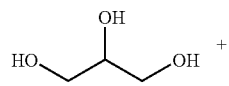
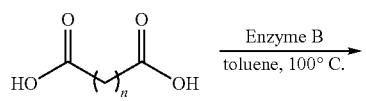
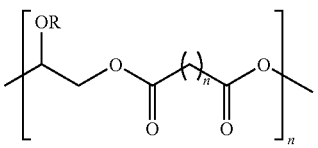

(b) poly(propane-1,2-diol-sebacate)

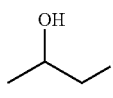
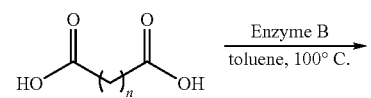
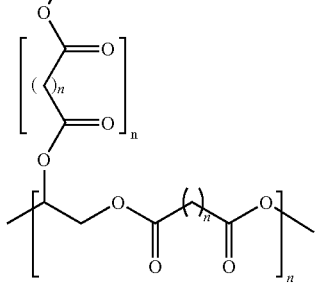

(c) poly(butane-1,3-diol-sebacate)

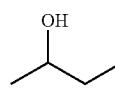
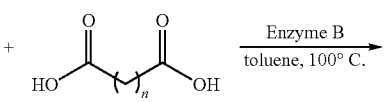

(d) poly(butane-2,3-diol-sebacate)

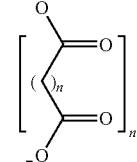
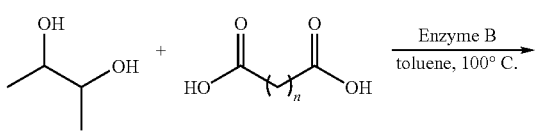
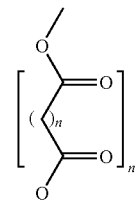

(e) poly(pentane-2,4-diol-sebacate)

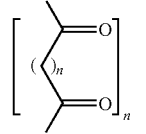
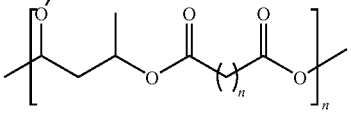

R : H or $\begin{bmatrix} \ce{(\ )}_n \end{bmatrix}_n$ n : 1~8

The polyhydric alcohol monomer having the secondary hydroxyl functional group used in the process of preparing the biodegradable polymer of the present invention is any one selected from the group consisting of glycerol, 1,2-propanediol, 1,3-butanediol, 2,3-butanediol and 2,4-pentanediol.

The acid monomer having the dicarboxylic group used in the process of preparing the biodegradable polymer of the present invention is any monomer containing dicarboxylic acid, and it is preferable to use sebacic acid in the present invention.

The enzyme catalyst used in the process of preparing the biodegradable polymer of the present invention is preferably lipase that is hydrolase. Particularly, *Candida antarctica* lipase B is preferable. The enzyme includes the amino acid of serine-histidine-aspartame (Ser-His-Asp). The enzyme may be prepared according to a known method, or a commercial product [Novozym 435 manufactured by Novo Nordisk Co. Ltd.] may be used. According to an instance of the method, *Candida* strains may be cultivated in a nutritive medium containing assimilable carbon and nitrogen sources, essential mineral matter, trace elements and the like under aerobic conditions, and the medium may be constructed in a conventional manner. After the cultivation, insoluble substances are removed by filtration or centrifuging to prepare a concentrated solution of liquid enzyme, and a culture solution may be subsequently evaporated or concentrated by reverse osmosis. The concentrated solution may be precipitated in a solvent capable of being mixed with salts or water, for example ethanol, or may be dried in a conventional spray manner to prepare a solid enzyme preparation.

It is preferable that the solvent used in the process of preparing the biodegradable polymer according to the present invention be selected from the group consisting of toluene and xylene, and it is preferable to use a solvent in which a substrate and a product are dissolved very well, and in which an enzyme has excellent stability and activity.

The biodegradable polymer prepared through the process according to the present invention is exemplified by poly(propane-1,2-diol-sebacate) (PPS), poly(butane-1,3-diol-sebacate) (PBS), poly(butane-2,3-diol-sebacate) (PBS) and poly(pentane-2,4-diol-sebacate) (PPS).

Since the biodegradable polymer according to the present invention is polymerized using the enzyme in the course of the polycondensation, it is easily prepared and friendly to nature, and it is possible to control a molecular weight depending on a reaction time in the course of the polymerization. Therefore, the biodegradable polymer is usefully applied to control the dose of a drug in a drug release system and is useful as a supporter for regenerating a desired biological tissue of a patient in tissue engineering.

A better understanding of the present invention may be obtained through the following examples and experimental example which are set forth to illustrate, but are not to be construed as the limit of the present invention.

Example 1

Production of poly(glycerol-sebacate) (PGS)

Glycerol (0.2 mol) was added to 30 ml of toluene containing sebacic acid (0.2 mol) dissolved therein, and then stirred in an argon atmosphere at 55° C. for one hour. After an enzyme B (5 wt %) was added as a catalyst, the mixture was allowed to react at 100° C. for 72 hours. Polycondensation was carried out using a dean-stark trap device. The resulting product was dried for 24 hours at reduced pressure.

Example 2

Production of poly(propane-1,2-diol-sebacate) (PPS)

The procedure of example 1 was repeated except that 1,2-propanediol was used instead of glycerol.

Example 3

Poly(butane-1,3-diol-sebacate) (PBS)

The procedure of example 1 was repeated except that 1,3-butanediol was used instead of glycerol.

Example 4

Poly(butane-2,3-diol-sebacate) (PBS)

The procedure of example 1 was repeated except that 2,3-butanediol was used instead of glycerol.

Example 5

Poly(pentane-2,4-diol-sebacate) (PPS)

The procedure of example 1 was repeated except that 2,4-pentanediol was used instead of glycerol.

Experimental Example

Structural Analysis of a Biodegradable Polymer According to the Present Invention Polymers prepared according to examples 1 to 5 were analyzed using $^1$H-NMR spectrum, $^{13}$C-NMR spectrum, G-IR spectrum, gel permeation chromatography (GPC), and thermogravimetric analysis (TGA).

1. $^1$H-NMR Spectrum, $^{13}$C-NMR Spectrum

The $^1$H-NMR spectrum was measured using 200 MHz and 400 MHz $^1$H-NMR spectrometers (Bruker, AVANCE 400).

1) Poly(glycerol-sebacate) [PGS]

$^1$H-NMR (200 MHz, CDCl$_3$) δ4.40-4.00 (m, —(C=O)OCH$_2$CH(OH)CH$_2$O(C=O)—), 4.00-3.60 (m, HOCH$_2$CH(OH)—), 2.35 (t, —OCC(C=O)CH$_2$—), 1.63 (m, —OCC(C=O)CH$_2$CH$_2$—), 1.31 (m, —(CH$_2$)$_4$—)

$^{13}$C NMR (CDCl$_3$) δ173.9, 70.2, 68.1, 65.1, 65.0, 53.4, 34.2, 34.0, 31.9, 29.6, 29.6, 29.3, 28.8, 24.7, 22.6, 14.0 (a peak at 173.9 ppm is a characteristic ester (C=O) peak of the synthesized polymer).

Shape of the polymer: hardened yellow solid

2) Poly(propane-1,2-diol-sebacate) [PPS]

$^1$H-NMR (200 MHz, CDCl$_3$) δ5.18 (m, methine H), 4.23 and 4.00 (m, —CH$_2$O (C=O)—), 2.29 (m, —OCC(C=O)CH$_2$—), 1.69 (m, —OCC(C=O)CH$_2$CH$_2$—), 1.30 (m, —(CH$_2$)$_4$—), 1.27 (d, J=6.5 Hz, —CH$_3$);

$^{13}$C NMR (CDCl$_3$) δ173.3, 173.1, 173.0, 67.9, 67.8, 65.9, 34.5, 34.4, 34.2, 29.1, 29.0, 28.0, 28.9, 24.9, 16.3 (peaks at 173.3, 173.1 and 173.0 ppm are characteristic peaks of ester).

Shape of the polymer: solid

3) Poly(butane-1,3-diol-sebacate) [PBS]

$^1$H-NMR (200 MHz, CDCl$_3$) δ5.00 (m, methine H), 4.08 (t, J=6.4 Hz, —CH$_2$BO(C=O)—), 2.26 (m, —OCC(C=O)

CH$_2$—), 1.84 (m, —OCH(CH$_3$)CH$_2$—) 1.58 (m, —OCC(C=O)CH$_2$CH$_2$—), 1.27 (m, —(CH$_2$)$_4$—), 1.21 (d, J=6.3 Hz, —CH$_3$);

$^{13}$C NMR (CDCl$_3$) δ173.6, 173.2, 67.5, 64.8, 61.5, 60.5, 38.0, 34.8, 34.5, 34.2, 34.1, 29.0, 24.9, 24.8, 23.4, 20.0 (peaks at 173.6 and 173.2 ppm are characteristic peaks of ester (C=O)).

Shape of the polymer: viscous colorless solution

4) Poly(butane-2,3-diol-sebacate) [PBS]

$^1$H-NMR (500 MHz, CDCl$_3$) δ4.96, 4.84 and 4.74 (m, —CHO(C=O)C—), 2.20 (m, —O(C=O)CH$_2$—), 1.59 (m, —O(C=O)CH$_2$CH$_2$—), 1.29 (m, —(CH$_2$)$_4$—), 1.17 (d, J=6.5 Hz, —CH$_3$);

$^{13}$C NMR (120 MHz, CDCl$_3$) δ173.5, 74.5, 34.5, 29.0, 28.0, 24.9, 14.1 (a peak at 173.5 ppm is a characteristic peak of ester (C=O)).

5) Poly(pentane-2,4-diol-sebacate) [PPS]

$^1$H-NMR (500 MHz, CDCl$_3$) δ5.13, 5.02 and 4.77 (m, —CHO(C=O)C—) 2.31 (m, —O(C=O)CH$_2$—) 2.00~2.80 (m, —OCHCH$_2$CHO—) 1.59 (m, —O(C=O)CH$_2$CH$_2$—), 1.28 (m, —(CH$_2$)$_4$—), 1.23 (d, J=6.5 Hz, —CH$_3$);

$^{13}$C NMR (120 MHz, CDCl$_3$) δ173.3, 65.8, 41.8, 34.5, 28.9, 24.8, 20.7 (a peak at 173.3 ppm is a characteristic peak of ester (C=O)).

2. Analyses Using G-IR Spectrum, Gel Permeation Chromatography (GPC) and Thermogravimetric Analysis (TGA)

The G-IR spectrum was measured using an FT-IR spectrophotometer (Thermonicolet, manufactured by Nicolet Inc.).

IR, GPC, and TGA results are illustrated in FIGS. 1, 2, and 3, respectively.

As shown in FIG. 1, biodegradable polymers prepared according to examples 1 to 5 were analyzed through FT-IR spectrum analysis, proving that characteristic peaks of the synthesized polymers were observed at 1740 cm$^{-1}$ (—C=O) and 28 cm$^{-1}$ (—CH), and thus, creation of the desired biodegradable polymer was confirmed.

As shown in FIG. 2, the biodegradable polymers prepared according to examples 1 to 5 were analyzed using gel permeation chromatography (GPC), proving that the number and weight average molecular weights of each synthesized polymer were 5000 and 15000, respectively. The analyzed polymer was a sample before it was purified.

As shown in FIG. 3, the biodegradable polymers prepared according to examples 1 to 5 were analyzed using the thermogravimetric analyzer (TGA), proving that a 10% weight loss of each synthesized polymer was achieved at 193° C., 233° C., 324° C., 257° C., and 242° C. for (a) poly(glycerol-sebacate), (b) poly(propane-1,2-diol-sebacate), (e) poly(butane-1,3-diol-sebacate), (d) poly(butane-2,3-diol-sebacate) and (e) poly(pentane-2,4-diol-sebacate), respectively.

As described above, the present invention provides a biodegradable polymer which is polymerized using an enzyme in the course of polycondensation, and thus, the biodegradable polymer is easily prepared and friendly to nature, and it is possible to control the molecular weight by varying the reaction time in the course of the polymerization. Thereby, the biodegradable polymer is usefully applied to control a dose of drug in a drug release system and is useful as a supporter for regenerating a desired biological tissue of a patient in tissue engineering.

What is claimed is:

1. A process of preparing a biodegradable polymer, comprising:
    polycondensating a polyhydric alcohol monomer having a secondary hydroxyl functional group and an acid monomer having a dicarboxylic group in the presence of a lipase in an organic solvent at 100° C. and using a Dean-Stark trap device,
    wherein
    the polyhydric alcohol monomer having a secondary hydroxyl functional group is selected from the group consisting of 2,3-butanediol and 2,4-pentanediol; and
    the polycondensation is carried out between the secondary hydroxyl functional group of the polyhydric alcohol monomer and the dicarboxylic group of the acid monomer.

2. The process as set forth in claim 1, wherein the acid monomer having a dicarboxylic group is sebacic acid.

3. The process as set forth in claim 1, wherein the enzyme catalyst is *Candida antarctica* lipase B.

4. The process as set forth in claim 1, wherein the organic solvent is toluene or xylene.

5. A process of preparing a biodegradable polymer, comprising:
    polycondensating a polyhydric alcohol monomer having a secondary hydroxyl functional group and an acid monomer having a dicarboxylic group in the presence of *Candida antarctica* lipase B in an organic solvent at 100° C. and using a Dean-Stark trap device to form a biodegradable polymer,
    wherein the polyhydric alcohol monomer having a secondary hydroxyl functional group is selected from the group consisting of 2,3-butanediol and 2,4-pentanediol;
    the lipase is 5 wt % of the total weight of the polyhydric alcohol monomer and the acid monomer;
    the acid monomer having a dicarboxylic group is sebacic acid; and
    the organic solvent is toluene or xylene.

6. The process as set forth in claim 1, wherein amount of the lipase is 5 wt % of the total weight of the polyhydric alcohol monomer and the acid monomer.

* * * * *